United States Patent
Kuorak et al.

(10) Patent No.: US 10,485,692 B2
(45) Date of Patent: Nov. 26, 2019

(54) SHOULDER ORTHOSIS

(75) Inventors: Lars-Ove Kuorak, Gällivare (SE);
Kurt Lennart Larsson, Malmberget (SE)

(73) Assignee: Ottobock SE & Co. KGaA, Duderstadt (DE)

( * ) Notice: Subject to any disclaimer, the term of this patent is extended or adjusted under 35 U.S.C. 154(b) by 272 days.

(21) Appl. No.: 12/670,790

(22) PCT Filed: Jul. 16, 2008

(86) PCT No.: PCT/SE2008/000452
§ 371 (c)(1),
(2), (4) Date: Feb. 26, 2010

(87) PCT Pub. No.: WO2009/017442
PCT Pub. Date: Feb. 5, 2009

(65) Prior Publication Data
US 2010/0210985 A1    Aug. 19, 2010

(30) Foreign Application Priority Data

Jul. 27, 2007 (SE) ........................ 0701792

(51) Int. Cl.
*A61F 5/00* (2006.01)
*A61F 5/37* (2006.01)

(52) U.S. Cl.
CPC .................. *A61F 5/3723* (2013.01)

(58) Field of Classification Search
CPC ........ A61F 5/3723; A61F 5/37; A61F 5/3738; A61F 13/14; A61F 13/146; A61F 5/373;
(Continued)

(56) References Cited

U.S. PATENT DOCUMENTS 4,559,932 A * 12/1985 Salort .................. A61F 5/0118
602/20
4,753,240 A * 6/1988 Sparks .......................... 607/108
(Continued)

FOREIGN PATENT DOCUMENTS

DE     G 92 15 341.0 U1    1/1993
DE         43 16 047 A1    11/1994
(Continued)

OTHER PUBLICATIONS

Neuro-Lux Orthosis No. 2-EU-601-7260, Description and Business News announcement, Dec. 1, 2005.

*Primary Examiner* — Victoria J Hicks
(74) *Attorney, Agent, or Firm* — Blank Rome LLP

(57) ABSTRACT

A shoulder orthosis (1) including a support portion (2) for positioning above a shoulder of user, which support portion exhibits a front (3) and a rear (4) portion which are formed so as to in use be positioned respectively in front of and behind a shoulder joint of the shoulder, a chest band (5) for connection to said front and rear regions and extending around a users chest in use, an arm cuff for application around an arm associated with the shoulder of the user, tension bands for connecting the support portion and the arm cuff. The arm cuff is a lower arm cuff (6) for positioning around said lower arm, the support portion (2) includes the upper arm cuff (7) for the positioning onto the upper arm of said arm, and said tension bands (8) join the upper arm cuff (7) and the lower arm cuff (6).

7 Claims, 2 Drawing Sheets

(58) Field of Classification Search
CPC ........ A61F 13/10; A61F 5/013; A61F 5/0118;
A61F 5/05858
USPC .......... 602/20, 19, 3, 5, 4, 1, 60, 61, 62, 63;
2/44, 45; 128/845, 846, 869, 878,
128/DIG. 19
See application file for complete search history.

(56) References Cited

U.S. PATENT DOCUMENTS

| | | | |
|---|---|---|---|
| 4,756,240 A * | 7/1988 | Mielke | 92/187 |
| 5,020,521 A | 6/1991 | Salort | |
| 5,181,906 A * | 1/1993 | Bauerfeind | A61F 13/10 |
| | | | 2/310 |
| 5,188,587 A * | 2/1993 | McGuire et al. | 602/20 |
| 5,235,675 A * | 8/1993 | Sudoh | 358/1.9 |
| 5,235,975 A * | 8/1993 | Gang | A61F 7/10 |
| | | | 128/875 |
| 5,403,268 A * | 4/1995 | Clement | A61F 5/3738 |
| | | | 128/DIG. 19 |
| 5,628,725 A * | 5/1997 | Ostergard | A61F 5/3746 |
| | | | 602/20 |
| 6,152,891 A * | 11/2000 | Carlson | 602/4 |
| 6,709,411 B1 * | 3/2004 | Olinger | 602/4 |
| 2003/0208146 A1 | 11/2003 | Kania | |
| 2008/0208092 A1 * | 8/2008 | Sawa | A61F 5/3738 |
| | | | 602/20 |

FOREIGN PATENT DOCUMENTS

| | | |
|---|---|---|
| DE | 201 14 446 U1 | 11/2001 |
| EP | 1609451 A1 | 12/2005 |
| FR | 20530 E | 5/1918 |

* cited by examiner

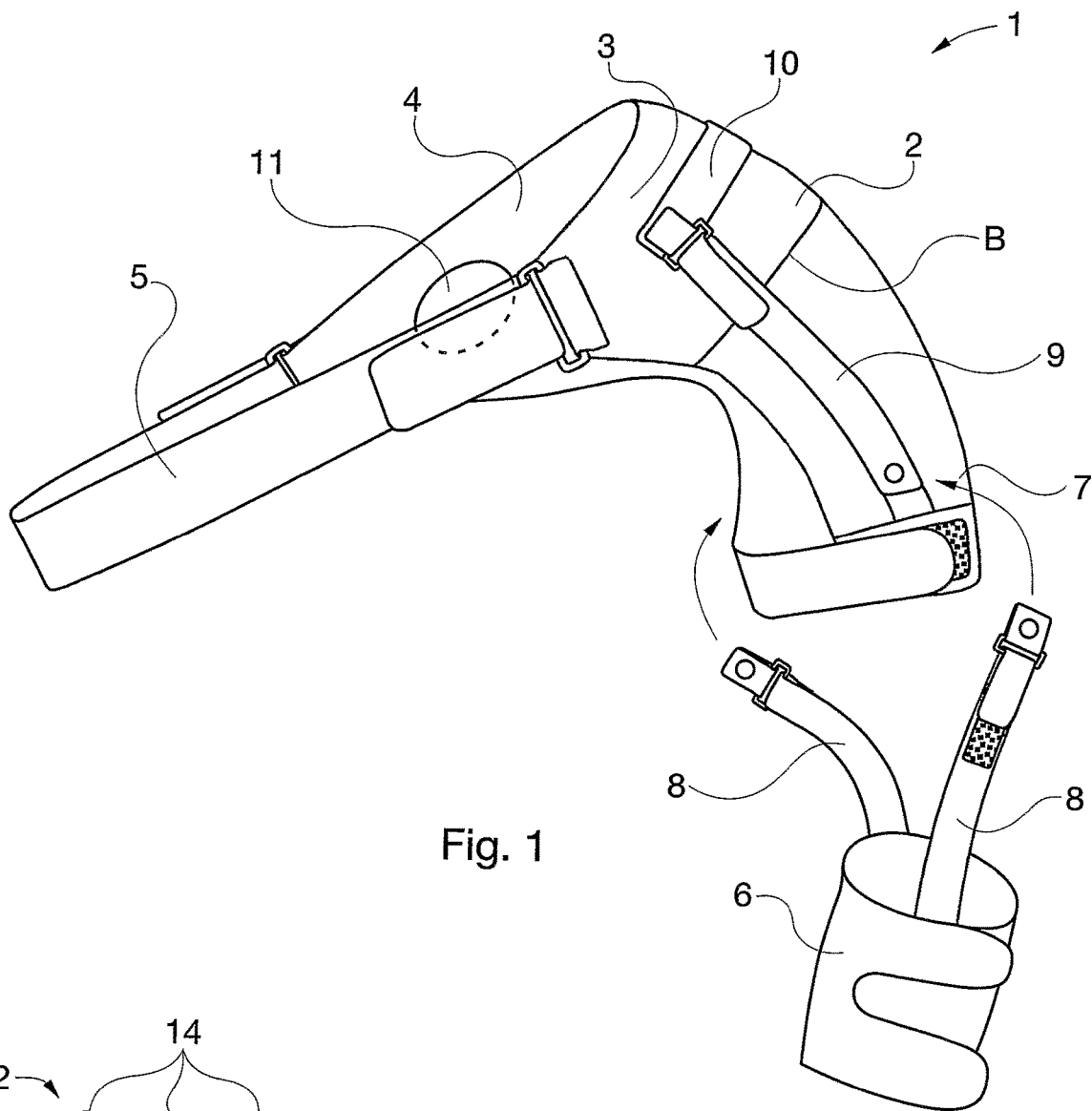
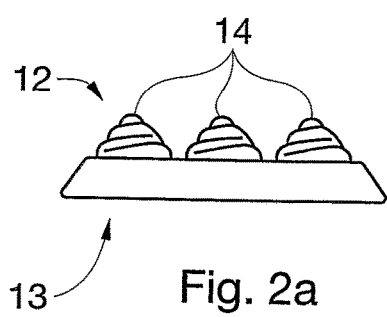
Fig. 2a
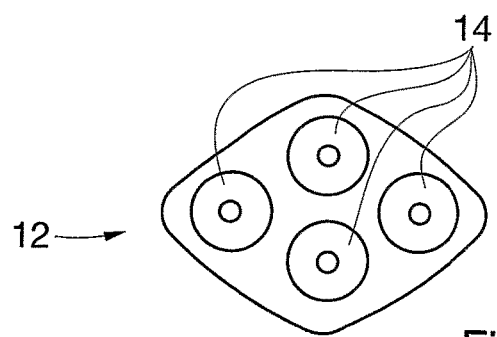
Fig. 2b

Fig. 3
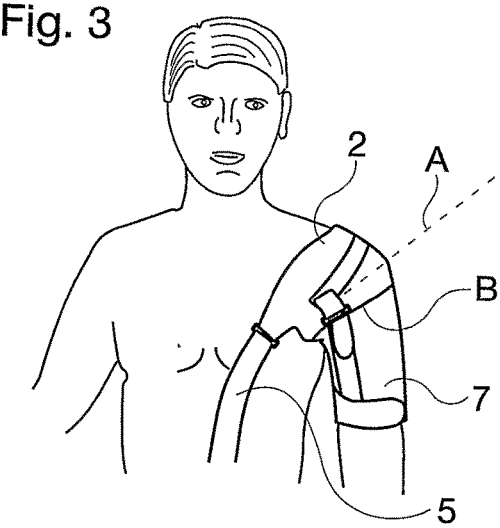
Fig. 4
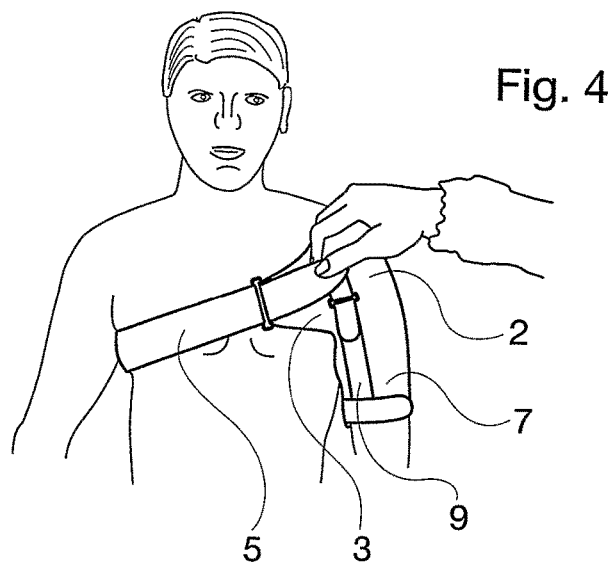
Fig. 5
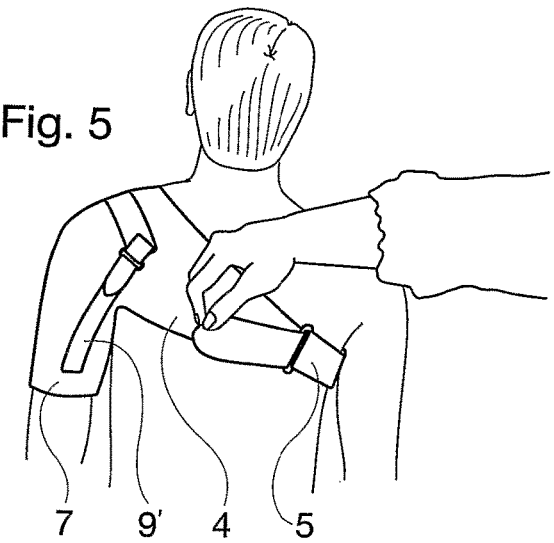
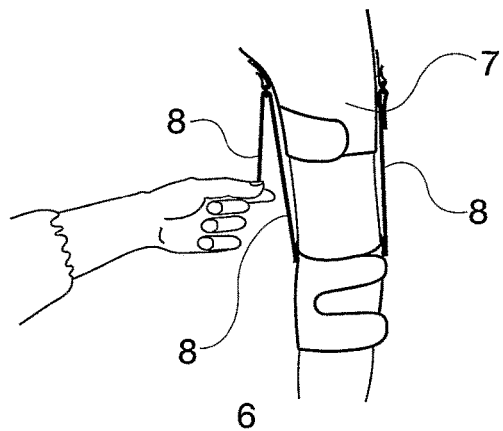
Fig. 6
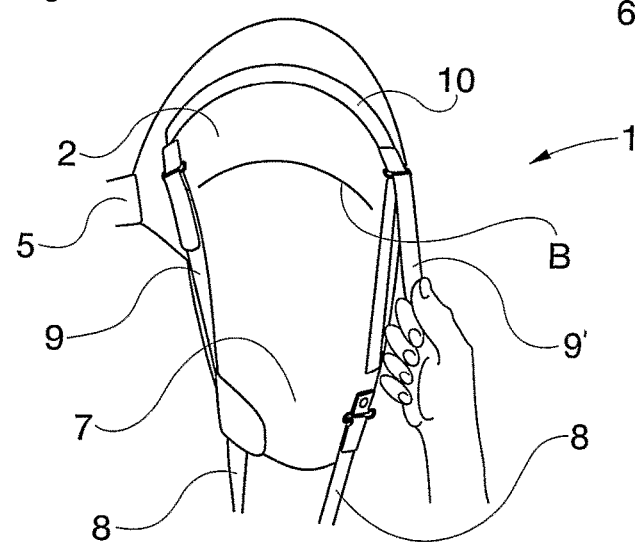
Fig. 7

SHOULDER ORTHOSIS

FIELD OF THE INVENTION

The invention concerns a shoulder orthosis according to the preamble of claim 1.

BACKGROUND OF THE INVENTION

Such a shoulder orthosis is known on the market and is intended for patients with indications such as shoulder pain and reduced function in the shoulder area.

The purpose of this orthosis is to provide relief of the shoulder portion and to allow increased movability for the arm concerned also for patients having reduced ability to move.

One problem with a previously known shoulder orthosis is that it allows limited possibilities of adjustment and reduces freedom of movement for user. For that reason, the previously known shoulder orthosis does not give entirely adequate support and relief in the conditions mentioned above.

As examples of background art can be mentioned U.S. Pat. No. 5,020,521 and FR 20 530 E (1:re Addition au Brevet d'Invention No: 486 552). These documents describe support devices which however, are not sufficiently flexible and adjustable.

AIM AND MOST IMPORTANT FEATURES OF THE INVENTION

It is an aim of the present invention to provide a shoulder orthosis as mentioned initially wherein the problems with devices according to the background art are at least reduced.

This is achieved with a shoulder orthosis exhibiting the features of claim 1. By including an upper arm cuff, increased stability for the entire orthosis is obtained and in particular for the support portion and thereby an increased supporting effect.

By further arranging a lower arm cuff, which is connected to the upper arm cuff through tension bands, increased freedom of movement is achieved for a user at the same time as a good support is afforded for the arm. By the support portion and the upper arm cuff being an integrated unit, simple handling and high stability is achieved. By at least one adjustable tension band being arranged between the support portion and the upper arm cuff advantageous adjustability is allowed also in this part of the orthosis.

It is preferred that at least any of the chest band, the lower arm cuff, the upper arm cuff and the tension band is adjustable. This gives good adjustment possibilities for adjustment to the single user.

It is preferred also that the number of said tension bands is two and starts from the respective front and rear areas for good freedom of movement and possibility of influencing movement of the arm.

It is further preferred that the support portion in the rear area provides means for placement of an inside positioned removable pressure pad for action against the shoulder portion of the user.

It is preferred that the orthosis includes a pressure pad for action against the shoulder area of the user.

Further features and advantages are obtained through further features of the invention, which will be clarified by the below description of an embodiment.

BRIEF DESCRIPTION OF DRAWINGS

The invention will now be explained in more detail by way of an embodiment and with reference to the annexed drawings, wherein:

FIG. 1 shows a shoulder orthosis according to the invention,

FIGS. 2a and 2b show a pressure pad for use in connection with the shoulder orthosis in FIG. 1, and FIGS. 3 to 7 show in a picture sequence positioning of a shoulder orthosis according to the invention onto a user.

DESCRIPTION OF EMBODIMENT

In FIG. 1 is shown, laid on a substrate, a shoulder orthosis 1, which includes a support portion 2 for positioning at and surrounding a shoulder area of a user. The support portion 2 includes a front region, which is intended to be positioned in front of shoulder joint of the user and a rear area 4 which is intended to be positioned at the rear of the shoulder joint and extending over the back across the spine.

The rear area is tapering from the main part of the support portion and has a length essentially corresponding to the major part of the user's back width.

5 indicates a chest band, which interconnects the free ends of the front region 3 and the rear region 4 such that the chest band 5 in use extends around the users chest under the armpit of the second arm.

The chest band can be tightened by means of Velcro© fastening devices in order to simply provide an individually adapted application.

An upper arm cuff 7 is integrated with the support portion 2 and extends, in use, along a part the upper arm of the user and has tightening means provided with Velcro© fastening devices. In the shown example, the tightening means are positioned at the free portion of the upper arm cuff 7, which is directed away from the shoulder. As illustrated in FIG. 1, the support portion 2 and the upper arm cuff 7 are contiguous, i.e., continuously connected without a break, and the upper arm cuff 7 entirely encircles the upper arm.

A lower arm cuff is indicated with 6. Like the upper arm cuff 7 it is provided with adjustable means in order to be tightened against the lower arm of the user. Like the upper arm cuff 7, the lower arm cuff 6 has tubular shape in use in a position where it is worn by a patient. The tightening means aim to tighten the respective cuff around the respective arm portion.

The lower arm cuff 6 is interconnected with the upper arm cuff 7 over two tension bands, which in principle are arranged diagonally to each other on the respective cuff. The tension bands 8 are provided with Velcro© fastening devices and are adjustable for simple adaption to the respective user.

9 indicates a tension band which acts between the front side of the upper arm cuff 7 and the front region of the support portion. A corresponding tension band, which is not shown in FIG. 1, is arranged on the rear portion of the upper arm cuff 7 and with its upper part of the rear region of the support portion (sees detail 9' in FIG. 5). These tension bands allow fine tuning of the adjustment.

A stabilizing band 10 extends between the front and the rear area above the shoulder of the user, in use of the orthosis.

On an extended portion of the rear region of the support portion 2 there is arranged an inwardly directed portion having a fastening region 11 with free-set loops of textile yards which are intended to cooperate with a pressure pad. In FIGS. 2a and 2b such a pressure pad 12 is shown, which on a rear side 13 is provided with Velcro© fastening devices for cooperation with said free-set loops in the fastening region 11.

The pad 12 has a contact surface with a number of pressure bosses 14 distributed over the surface. On the shown pad 12 four such pressure bosses 14 are arranged, which have the function of acting against a shoulder portion of a user for stimulating purposes. In particular, stimulation is intended of weak muscles between the shoulder blade and the spine of a patient.

FIGS. 3 to 7 are intended to illustrate the process of positioning a shoulder orthosis according to the invention onto a user. In FIG. 3, the shoulder orthosis 1 has been put on the shoulder of the user with an initial position of the support portion 2 somewhat below its using position. The interrupted line A indicates the so called joint slot. A seam B at the upper arm cuff should in an adjusted position, in use, be just about in line with the line A. The upper arm cuff 7 is tightened by means of an overlapping tension band provided with Velcro band around the upper arm of the user.

In FIG. 4 is illustrated tightening and adjustment of the chest band 5 on the front side of the user's chest.

FIG. 5 illustrates adjustment of tightening at the rear portion of the chest band. This adjustment and associated tightening arrangement is optional.

All in all, the tensioning of the chest band 5 results in inward and upward pulling of the support portion 2 and thereby lifting of the entirely shoulder portion including the upper arm.

In FIG. 6 is illustrated the lower arm cuff 6, which in the shown position tightened and fixed to the lower arm of the user. Further is shown tightening of the tension bands 8 on each side of the respective upper arm cuff and the lower arm cuff. The aim is to obtain a relief of the elbow joint and the muscles controlling the lower arm with maintained high movability of the user's lower arm.

It should be noted that the construction with tension bands, in the shown example two tension bands, gives great opportunities for individual adjustment of the position of the lower arm cuff. Through the positioning of the tension bands, in practice, the rotational position of the lower arm cuff in respect of the upper arm cuff providing further the possibility so as to achieve a desired twisting effect to the lower arm. Normally, as a rule an outward rotation effect of the lower arm cuff is desired, and thereby of the entire arm in respect of the support portion and the shoulder.

FIG. 7 illustrates the tightening of the tightening bands 9, 9' for achieving a final adjustment of the orthosis.

In the figure sequence 3-7 is shown the user being helped with applying of the orthosis. For patients being seriously disabled this is the normal procedure. It is, however, not excluded that many patients can handle positioning and removal of a shoulder orthosis according to the invention themselves.

The invention can be modified within the scope of the following claims. The tightening function can thus be achieved otherwise and through bands with cooperating Velcro© fastening devices, for example with conventional band buckles, even if Velcro© fastening devices are preferred in respect of the invention. It is, however, not excluded that an orthosis according to the invention is entirely adapted to a particular user, whereby in such a case the need for adjustability possibilities can be excluded for one or more of the above shown tightenable details.

The support portion can be constructed without a fastening region for a pressure pad and it is also possible to arrange an upper arm cuff, which is not an integrated unit of the support portion. This solution is, however, not preferred in respect of the invention. It should also be noted that the orthosis can be used without the lower arm cuff being connected.

The main parts (other than the tension bands, which are inelastic) of the shoulder orthosis should be made from suitable elastic materials in order to achieve the desired freedom of movement with movement promoting support for the orthosis. Such materials can for example be elastic, so called 3-D-materials, or elastic neoprene rubber, laminated with suitable flexible textile materials on the inside as well as on the outside of the support portion as well as the upper arm cuff and the lower arm cuff. It is preferred that an elastic, PCM-material containing layer (Phase Change Material) such as for example PCM foam material will come to use in order to allow a temperature regulating effect. The pad can be manufactured from many different synthetic materials. One example is thermoplastic polyurethane.

On the inside of the cuffs, typically close to the edges, at the greatest distance from the shoulder joint, there are preferably arranged friction increasing strips of silicon rubber in order to reduce tendencies of sliding between the cuffs and parts of the arm.

The invention claimed is:

1. A method of providing relief to a shoulder and allowing movability of a lower arm of a user by positioning a shoulder orthosis onto a user, the shoulder orthosis including:
a support portion adapted to be positioned above a shoulder of the user, said support portion comprising a front and a rear region that are formed so as to be positioned, in use, respectively in front of and behind a shoulder joint, the rear region tapering from a main part of the support portion;
a chest band for connection, in use, to free ends of said front and rear regions and extending around a user's chest;
a lower arm cuff adapted to be positioned around the lower arm of the user, the lower arm being associated with the shoulder of the user, the lower arm cuff having a tubular shape in use in a position where it is worn by the user, the lower arm cuff being provided with adjustable means to be tightened against the lower arm of the user;
an upper arm cuff adapted to be positioned onto an upper arm of said user, wherein the upper arm cuff is a tubular structure that is adapted to entirely encircle the upper arm, said upper arm cuff having front and rear regions, said upper arm cuff extending in use along a part of the upper arm and is provided with tightening means positioned on a free portion of the upper arm cuff and directed away from the shoulder to completely encircle said upper arm and allow the upper arm cuff to be tightened against the upper arm of the user, wherein the upper arm cuff is integrated with the support portion so that the support portion and the upper arm cuff form an integral unit, wherein the upper arm cuff and the support portion are continuously connected with each other and without a break between the upper arm cuff and the support portion, and wherein at least one adjustable tension band is arranged between the support portion and the upper arm cuff; and
two tension bands connecting the upper arm cuff and the lower arm cuff, the two tension bands being inelastic, and arranged diagonally to each other on respective cuff,
wherein said two tension bands connecting the upper arm cuff and the lower arm cuff are two individual bands and extend, respectively, from the front and rear regions of the upper arm cuff to the lower arm cuff in order to obtain relief of an elbow joint and muscles controlling the lower arm while maintaining high movability of the user's lower arm, the tension bands being positioned so that rotational position of the lower arm cuff in respect to the upper arm cuff provides the possibility to achieve a desired twisting effect of the lower arm;

the method comprising the steps of:

putting the shoulder orthosis on the shoulder of the user and tightening the upper arm cuff around the upper arm of the user;

tightening and adjusting the chest band on the user's chest;

positioning the lower arm cuff around the lower arm of the user, and tightening the lower arm cuff against the lower arm of the user;

tightening the two tension bands connecting the upper arm cuff and the lower arm cuff, thereby obtaining relief of the elbow joint and muscles controlling the lower arm while maintaining high movability of the user's lower arm, the two tension bands connecting the upper arm cuff and the lower arm cuff allowing rotation of the lower arm cuff in respect to the upper arm cuff and thereby allowing the desired twisting effect of the lower arm.

2. The method according to claim 1, wherein at least one component from the group consisting of: the chest band, the lower arm cuff, the upper arm cuff, and the tension bands; is tightenably adjustable.

3. The method according to claim 2, wherein said at least one component is provided with any one from the group consisting of: (1) a band with hook and loop material fastening means, and (2) a band with a buckle.

4. The method according to claim 1, wherein the shoulder orthosis includes main parts, and wherein the main parts of the shoulder orthosis include elastic material in order to obtain freedom of movement with movement promoting support.

5. The method according to claim 4, wherein said elastic material is any one of the group: elastic 3-D-material, elastic neoprene rubber, PCM material, PCM foam material.

6. The method according to claim 1, wherein the support portion in the rear region is arranged for placement of an inside positioned removable pressure pad for action against a shoulder region of the user.

7. The method according to claim 1, wherein the shoulder orthosis includes a pressure pad for action against a shoulder region of the user.

* * * * *